(12) United States Patent  (10) Patent No.: US 7,575,603 B2
Bergin et al.  (45) Date of Patent: Aug. 18, 2009

(54) FLUTED INTRAMEDULLARY STEM

(75) Inventors: Alisha Bergin, Southaven, MS (US); David C. Kelman, Collierville, TN (US); Richard D. Lambert, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 392 days.

(21) Appl. No.: 11/139,926

(22) Filed: May 27, 2005

(65) Prior Publication Data

US 2006/0004465 A1   Jan. 5, 2006

Related U.S. Application Data

(60) Provisional application No. 60/575,636, filed on May 28, 2004, provisional application No. 60/655,129, filed on Feb. 22, 2005.

(51) Int. Cl.
*A61F 2/36* (2006.01)
*A61F 2/38* (2006.01)

(52) U.S. Cl. ............... 623/23.31; 623/20.36; 623/20.34

(58) Field of Classification Search ............... 623/22.42, 623/23.29, 23.31, 23.26, 23.44, 23.35, 20.36, 623/23.23, 23.24, 20.34, 22.4, 22.43, 22.46, 623/23.15, 23.18, 23.33, 23.34; 606/62, 606/67

See application file for complete search history.

(56) References Cited

U.S. PATENT DOCUMENTS

| | | | |
|---|---|---|---|
| 3,067,740 A | 12/1962 | Hoboush | |
| 4,516,277 A | 5/1985 | Butel | |
| 4,661,112 A | 4/1987 | Muller | |
| 4,756,711 A | 7/1988 | Mai et al. | |
| 4,808,186 A | 2/1989 | Smith | |
| 4,944,761 A | 7/1990 | Stuhmer et al. | |
| 4,986,834 A | 1/1991 | Smith et al. | |
| 5,100,407 A | 3/1992 | Conrad et al. | |
| 5,171,323 A | 12/1992 | Willert et al. | |
| 5,336,265 A | 8/1994 | Serbousek et al. | |
| 5,507,829 A | 4/1996 | Thongpreda et al. | |
| 5,509,935 A | 4/1996 | Fosco et al. | |
| 5,549,702 A | 8/1996 | Ries et al. | |
| 5,593,446 A * | 1/1997 | Kuoni | 623/23.44 |
| 5,702,482 A | 12/1997 | Thongpreda et al. | |
| 5,755,805 A * | 5/1998 | Whiteside | 623/23.24 |
| 5,776,204 A | 7/1998 | Noble et al. | |
| 6,554,865 B2 | 4/2003 | Grusin et al. | |
| 2002/0120344 A1 | 8/2002 | Meulink et al. | |
| 2004/0002759 A1 * | 1/2004 | Ferree | 623/17.11 |
| 2004/0006392 A1 | 1/2004 | Grusin et al. | |

FOREIGN PATENT DOCUMENTS

| | | |
|---|---|---|
| DE | 19725773 | 12/1998 |
| EP | 145938 | 6/1985 |
| EP | 0 159 462 A1 | 10/1985 |
| EP | 0 623 321 A1 | 11/1994 |

(Continued)

*Primary Examiner*—Paul Prebilic
*Assistant Examiner*—Joshua Levine
(74) *Attorney, Agent, or Firm*—Kilpatrick Stockton LLP (57) ABSTRACT

An intramedullary stem that provides enhanced distal fixation and flexibility and methods for implanting the stem. Certain embodiments of the stem have primary and secondary flutes (or ridges or wedges). Other embodiments have transitional regions.

18 Claims, 4 Drawing Sheets

FOREIGN PATENT DOCUMENTS

| | | |
|---|---|---|
| EP | 0 668 064 A1 | 8/1995 |
| EP | 0 709 071 A2 | 5/1996 |
| EP | 0 709 071 A3 | 5/1996 |
| EP | 1 698 304 A1 | 9/2006 |
| FR | 2483218 | 12/1981 |
| FR | 2 643 256 | 8/1990 |
| WO | WO 00/02504 | 1/2000 |

* cited by examiner

FLUTED INTRAMEDULLARY STEM

This application claims benefit of U.S. Provisional Patent Application Ser. No. 60/575,636 titled "Modular Hip Stem with Cylindrical Flutes and Tapered Core" filed May 28, 2004 and U.S. Provisional Patent Application Ser. No. 60/655,129 titled "Fluted Cylindrical Hip Stem with Tapered Core" filed Feb. 22, 2005, the entire contents of each of which are hereby incorporated by reference.

FIELD OF THE INVENTION

The present invention relates, in general, to intramedullary implants and stems, and particularly hip stems, that are provided to replace worn joints.

BACKGROUND

Artificial implants, including hip joints, shoulder joints, and knee joints, are widely used in orthopedic surgery. Artificial hip and shoulder joints are generally ball and socket joints, designed to match as closely as possible the function of the natural joint. To duplicate a joint's natural action, a total joint replacement implant has three parts: the stem, which fits into the femur or humerus and provides stability; the ball, which replaces the spherical head of the femur or humerus; and the cup, which replaces the worn-out hip or shoulder socket.

There are many types of stems that may be used in joint replacement surgery to secure the artificial ball that will articulate with the artificial socket. Some stems are modular, allowing a greater range of options during the surgery. Each part comes in various sizes in order to accommodate various body sizes and types. In some designs, the stem and ball are one piece; in other designs, they may be provided as separate pieces. In further designs, the stem and ball may feature a modular body, a removable neck, or any combination of these or additional features. Such designs and their combinations will be referred to throughout this document as "modular," and are intended to allow for additional customization and fit.

Specifically, modular stems may be provided in any number of lengths and widths. Corresponding modular bodies and heads may be provided in various sizes, allowing the surgeon to select the best options for the particular patient. Other stems may be non-modular, and may provide a stem, neck, and ball in a one-piece configuration.

In choosing a proper implant, the surgeon will consider individual patient needs. One consideration may be modularity; another consideration may be stability needed based on proximal bone degeneration that may have already taken place. If there is substantial bone degeneration, the surgeon will likely choose a stem with additional distal fixation features to prevent any more proximal bone erosion. In other words, the surgeon must seek supportive bone more distally, rather than relying on support from the proximal bone. This is particularly an issue in revision surgeries, although it may also be a concern during a primary surgery. Accordingly, there is a challenge to provide stems that are stable and provide efficient loading for distribution and implant longevity, but that also allow the surgeon as may options as possible.

The two current, but different, distal femoral fixation philosophies include relying on (a) a cylindrical coated stem (the coating may be a biological coating or a bead coating, described more fully below) or (b) a tapered grit-blasted stem. Both types of stems have disadvantages.

Some surgeons using traditional, conical, tapered hip stems find it difficult to recreate the femoral neck height because the stem locks into place within the femoral canal too high or too low. The primary factors resulting in stem placement uncertainty are the difficulty in reproducible reamer depth placement and variations in bone quality. Some revision tapered hip stems offer modular necks of various heights to compensate for the difficulty, but offering modular necks as the sole solution may increase the complexity of the surgical procedure.

Cylindrical biologically and/or bead coated revision hip stems have the advantage of a more reproducible fit during the surgery. However, the biological enhancement coating in conjunction with the cylindrical shape of the implant may cause stress-shielding to the proximal bone due to the concentration of loading forces in the mid to distal portion of the stem. (Unlike a tapered stem, a cylindrical stem loads the bone entirely against shear forces within the femoral canal. The inefficient loading distribution likely causes bone loss proximally, making future revision surgeries even more difficult.)

Cylindrical stems are typically bowed stems. Recently, another design that has been explored is a tapered stem with a cylindrical bow at its distal end. When seeking support for the prosthesis more distally, a surgeon may alternatively use a longer revision stem. With long stems, the most distal section of the stem must be modified to accommodate the anterior bow of the femur. This is because, although a longer stem can provide additional stability, the length of the stem could perforate the cortex of the femur during insertion if the stem is not slightly curved to follow the natural curve of the femur. Current options for modifying the stem are bowing, angling, or otherwise shaping the distal section of the stem to follow the natural curve of the femur, or adding a chamfer slot in the stem. Accordingly, although bowed stems can provide increased stability, they can limit stem neck orientation options because the one-piece options do not always provide the modularity that may be desired at times due to the stem being limited to being orientated in the proper direction of the bow. If an independent body and/or neck portion is provided for use with the stem, orientation options may be increased, but as mentioned, this may also increase the complexity of the surgery.

Other stems designs seek to provide additional stability by offering bone in-growth or bone on-growth surfaces. These surfaces can be physically formed by roughening the stem surface, providing metallic beads, grit blasting, or forming a porous surface in the stem surface such that it supports bone growth. Additionally or alternatively, the surface of the implant may be provided with hydroxyapatite or any other biological substance that promotes bone in-growth or on-growth.

Other attempts to provide stems with greater stability have included providing grooves at certain areas on the shaft portion. The grooves are typically intended to vary the stiffness along the stem shaft to provide stiffness and stability in some areas but less stiffness in other areas.

However, there is a need in the art to provide an intramedullary stem that provides strong distal fixation (particularly for revision surgeries when there is not much bone at the proximal portion of the bone). There is also a need for a stem with the desired distal fixation, but that also provides flexible options that are not limited by stem length and the requirement of a bowed portion at the distal end of the stem. There is also a need for a stem that has axial and rotational stability, while also providing a certain amount of flex. There is also a need for a stem that provides increased surface area for bone in-growth and/or on-growth.

SUMMARY

Certain embodiments of the present invention provide intramedullary stems for particular use in hip joint replacements that provide enhanced distal fixation and flexibility. Certain embodiments of the stems may have primary and secondary flutes (or ridges or wedges). Other embodiments have transitional regions.

DETAILED DESCRIPTION

Intramedullary stems developed for enhanced distal stabilization are often formed as cylindrical stems, grit-blasted tapered stems, or long stems (which are often necessarily bowed due to their use and the patient's anatomy.) All of these stems have drawbacks. For example, most bowed stems limit the surgeon's ability to orient the stem; if it is not modular, the stem can only be implanted such that the bow corresponds to the natural curve of the patient's bone. Accordingly, the present invention provides an alternate to current stems, while still providing enhanced distal fixation, modularity options, enhanced stabilization, and flexibility.

Figure 1:
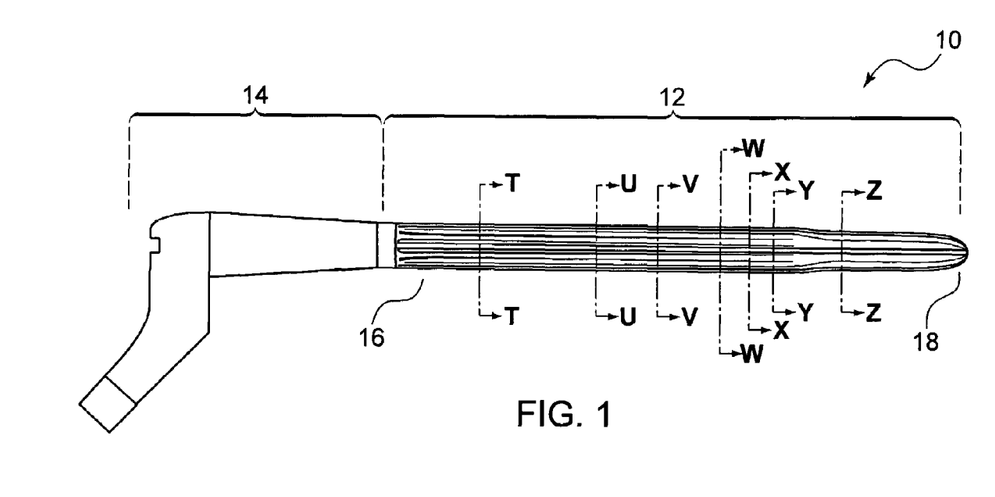
FIG. 1 shows a side plan view of a stem according to certain embodiments of the invention.
Figure 7:
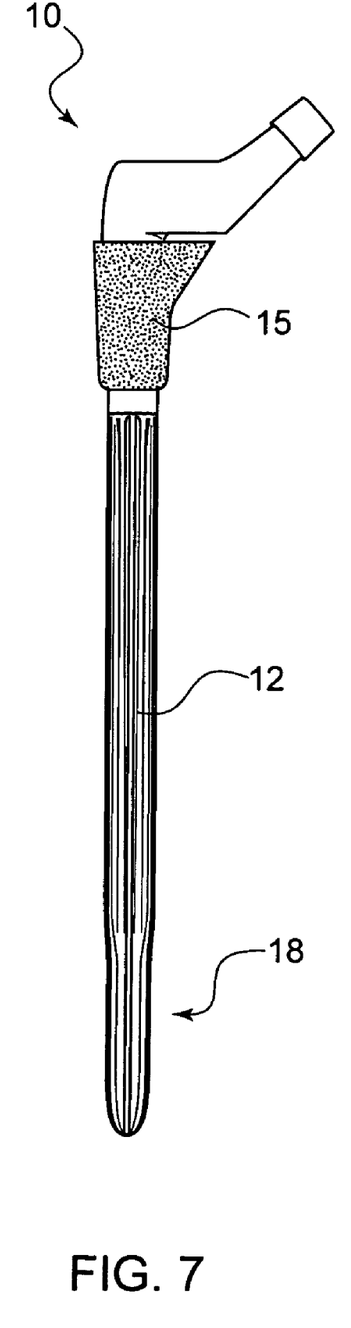
FIG. 7 shows a side view of one embodiment of a modular stem according to various embodiments of the invention.

As shown in FIG. 1, stems 10 according to certain embodiments of the invention have a shaft 12 with a longitudinal length and an upper stem portion 14. The upper stem portion 14 is adapted to receive a ball or head (not shown) to articulate with an artificial socket. Alternatively, the stems 10 described herein may be used in connection with a modular proximal body and/or a modular neck to provide the upper stem portion 14 of the stem 10, such that the shaft 12 and upper stem portion 14 are provided as a multi-piece configuration to allow independent sizing if desired. If provided, a modular body may be provided in the form of a sleeve 15 that slides over the distal end 18 of shaft 12, as shown in FIG. 7. Sleeve 15 may be any number of sizes, to provide the surgeon with a greater degree of flexible options during the surgery.

Although the sleeve (or modular body) may be solid, it may also be grit-blasted or have another surface treatment. It is also possible for the sleeve or modular body to have longitudinal grooves for reduced stiffness to more effectively load the femur. The grooves may be any shape or configuration. In certain embodiments, the grooves are formed using any of the design concepts described below, such as primary flutes, secondary flutes, wedges, ridges, cross-sectionally tapered flutes, substantially parallel-sided flutes, longitudinally tapering flutes, or narrowing apex flutes.

Figure 4:
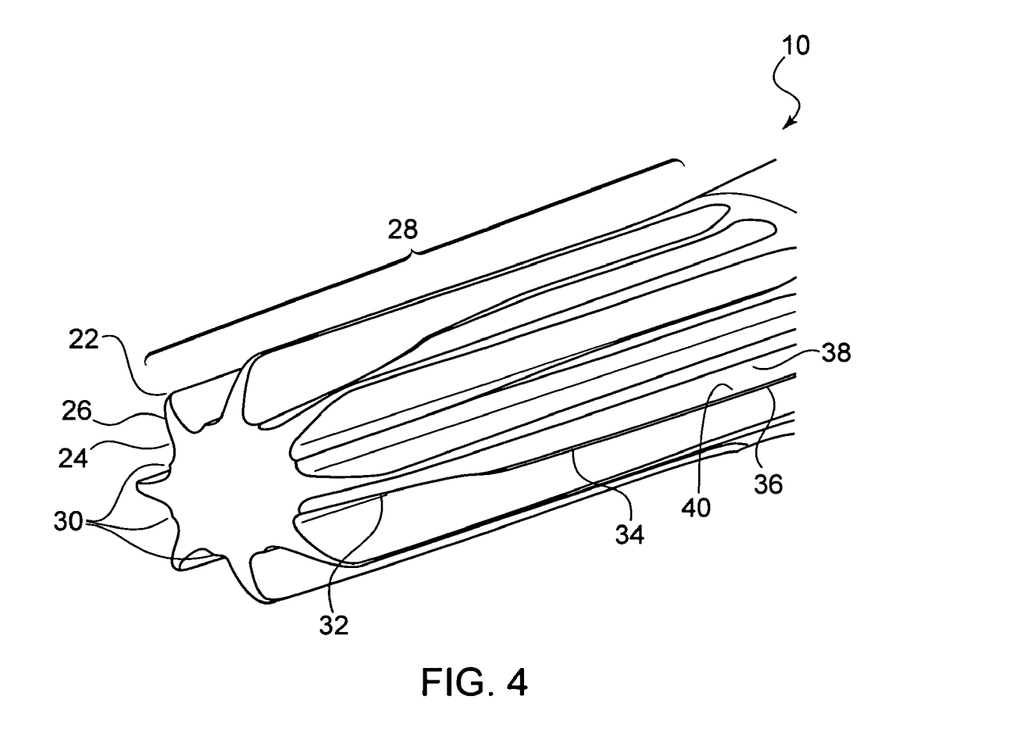
FIG. 4 shows a close-up perspective view of the distal portion of a stem according to certain embodiments of the invention.

The shaft 12 has a proximal end 16 and a distal end 18. The distal end 18 is adapted to be inserted into a patient's intramedullary canal to secure the stem in place. It may be flat, rounded, bullet-nosed (as shown), or any other useful configuration. The length of shaft 12 is shown having a series of flutes 20. The series of flutes 20 is provided, among other things, for rotational and axial stability. FIG 4 shows certain flutes on the stem 10 that are formed in a triangular cross-sectional shape, with each flute having an apex 22, a base 24, and tapering sides 26. This formation will be referred to as being cross-sectionally tapered, because of the configuration of tapering sides 26. (Although an apex is typically thought of as a point where two sides meet, the flute apexes described herein need not be a point; it may be rounded, square, or any other shape. The term is being used to refer to the outermost portion of the flute.) Although not shown, it is also possible for flutes to have parallel (or substantially parallel) sides rather than tapered sides. This formation will be referred to substantially parallel-sided flutes. Cross-sectionally-tapered flutes add extra support against stem subsidence, but substantially parallel-sided flutes or a combination of substantially parallel sided and cross-sectionally tapered flutes may also be used. The flutes may also provide support against rotation. It is also possible for a single flute to have both cross-sectional taper and parallel-sided features at different points along its length.

Another type of tapering that the series of flutes 20 may have is a narrowing apex. A narrowing apex may be featured on a cross-sectionally tapered flute or a parallel-sided flute. A flute with a narrowing apex may have a base 24 that maintains a similar size throughout the length of the flute but an apex 22 that narrows as the flute extends longitudinally, and that preferably narrows from the proximal end to the distal end of the stem. This narrowing may be a smooth narrow (i.e., a traditional taper), or it may be a stepped narrowing (like sawtooth or a series of ledges, having substantially straight sides.)

Figure 2:
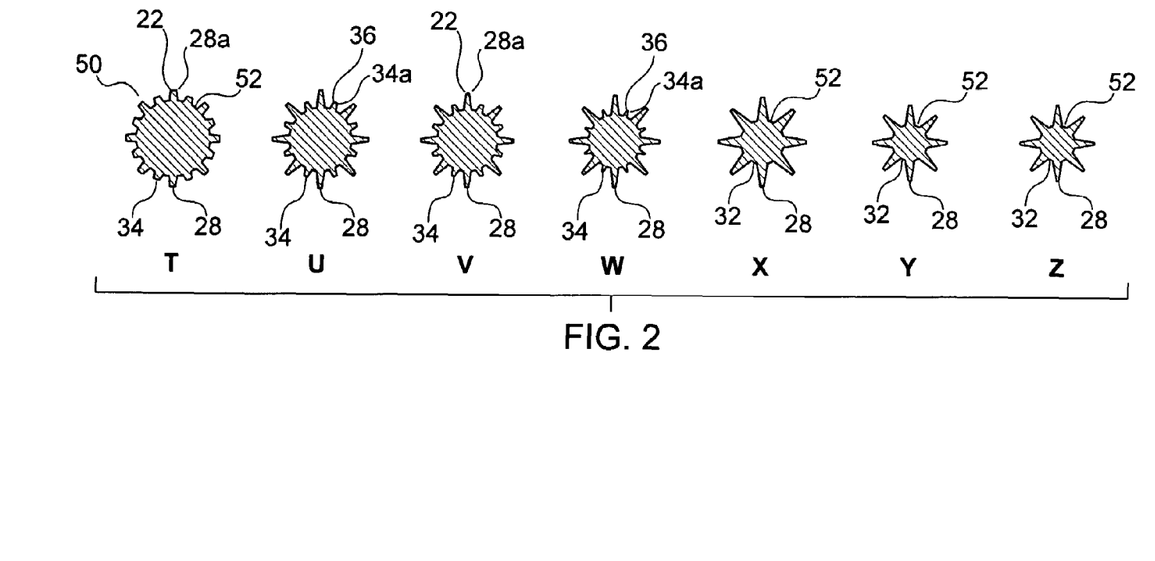
FIG. 2 shows various cross sections of the stem of FIG. 1 that correspond by letter to cross sections indicated on FIG. 1.

For example, the flute 28A shown in FIG. 2 appears to have a relatively flat apex 22 in cross section T. The apex narrows to a tapered point in cross sections V-Z. If provided, the narrowed apex preferably narrows as the flute extends longitudinally distally (as shown in FIG. 4), although, if desired, the apex may narrow as the flute extends proximally instead.

In certain embodiments, flutes having the described configurations may extend the substantial length of the shaft 12 or any part of shaft, and will be referred to as primary flutes 28. The apexes 22 of primary flutes 28 (whether or not they are provided as narrowing apexes) define an outer profile 50 of stem shaft, as shown in FIG. 2. Outer profile 50 may have a substantially constant diameter along the shaft 12, it may taper as it extends longitudinally, or it may be oval, oblong, rectangular, or any other desired configuration. In preferred embodiments, the outer profile 50 is preferably cylindrical (or substantially cylindrical) and maintains a similar diameter throughout much of the length of the shaft 12, although the outer profile 50 may slightly decrease in size or taper longitudinally toward the distal end 18 of the stem.

The bases 24 of primary flutes 28 define an inner profile 52 (or core) of stem shaft 12. Inner profile 52, as opposed to the embodiment with an outer profile of relative constant diameter, preferably tapers as it extends longitudinally and distally, also shown in FIG. 2, also this is not required and other profiles are possible. This tapered core 52 allows additional surface area of the flutes to be exposed, increasing the flutes' ability to "grab" into bone. In essence, the flutes 28 form ledges or wedges that may be used to grab the sides of the femoral canal for enhanced stability.

Figure 3:
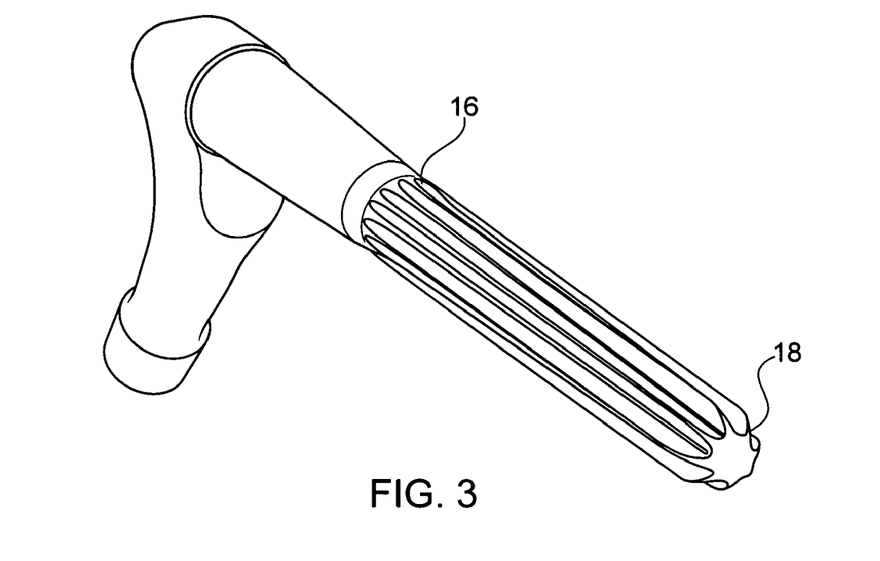
FIG. 3 shows a side perspective view of a stem according to certain embodiments of the invention.
Figure 5:
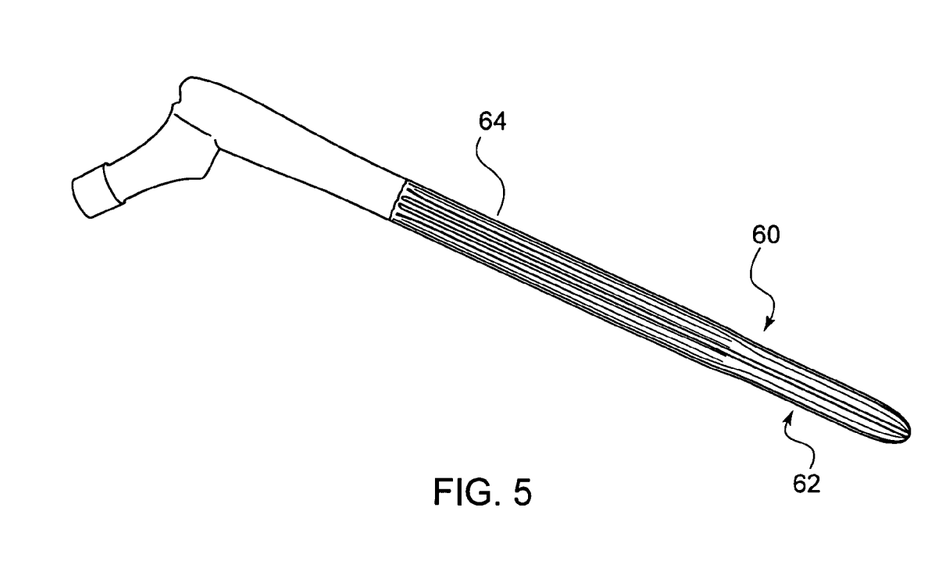
FIG. 5 shows a side perspective view of a stem according to further embodiments of the invention.

Another type of flute that optionally may be provided on stem 10 is secondary flute 34. Secondary flutes 34 may be be provided in any of the above-described configurations, and they are preferably provided at a different level than primary flutes 28. For example, as shown in FIGS. 3 and 5, secondary flutes 34 may have an apex 36 that is shorter or less pronounced than primary flutes 28. This shortening may be a stepped down-type configuration (e.g., an angled sawtooth profile), or the flutes may taper in the longitudinal direction as they extend down the stem. Alternatively, the flutes may maintain a constant shape throughout their length. Preferably, secondary flutes taper longitudinally as they extend distally down shaft, as shown in the cross-sections of FIG. 2. Preferably, they also have a narrowed apex 36 (similar to the narrowed apex embodiment for primary flutes 28) as shown by the secondary flute 34A in cross sections U and W. In cross section U, the apex is relatively blunt and in cross section W, the apex has narrowed to more closely resembled a point or some other narrowed portion.

Additionally, as with primary flutes, secondary flutes 34 may be cross-sectionally tapered or substantially parallel-sided. They may extend the substantial length of shaft or any part of shaft.

FIG. 4 shows one embodiment of a potential configuration of secondary flutes 34. In this Figure, the bases 24 of two primary flutes 28 may meet to form a valley 30. In certain embodiments, a valley 30 at the distal end 18 of shaft may be V-shaped, a U-shaped, rounded, curved, or any other desired valley shape where the bases 24 of tapering sides 26 (or substantially parallel sides) of the primary flutes 28 meet. In other embodiments, a valley 30 at the distal end 18 of shaft may have a slight ridge 32, as shown in FIG. 4. Slight ridge 32 is the very tip of what may be a secondary flute 34. Secondary flutes 34 may begin at the proximal end 16 of shaft, along with primary flutes 28, and although they may be similar in size and shape to primary flutes 28, they are preferably provided a different level than primary flutes 28, and even more preferably, the are at least slightly smaller than primary flutes 28. They may have an apex 36, a base 38, and tapering sides 40. This formation will be referred to as being cross-sectionally tapered, because of the configuration of tapering sides 40. Although not shown, it is also possible for secondary flutes 34 to have parallel (or substantially parallel) sides rather than tapered sides. That formation will be referred to as substantially parallel-sided flutes. As with primary flutes, cross-sectionally-tapered secondary flutes also add extra support against stem subsidence, but parallel (or substantially parallel) sided flutes or a combination of substantially parallel sided and cross-sectionally tapered flutes may also be used. The flutes may also provide support against rotation. It is also possible for a single flute to have both cross-sectional taper and parallel-sided features at different points along its length.

In certain preferred embodiments, as secondary flutes 34 extend toward distal end 18, they begin to taper out longitudinally (which will be referred to as a longitudinal taper). In other words, the apex 36 of the secondary flute 34 is smaller (meaning that its height can be shorter in relation to the core) at the apex at the distal end 18 than it is at the proximal end 16. (In another embodiment, the term smaller may be used to refer to a smaller narrowed apex, if provided.) This can be seen by the illustration at FIG. 2, which shows various cross sections of the shaft of FIG. 1 and how the core 52 tapers as the stem extends distally. In addition to showing the secondary flutes 34 longitudinally tapering, FIG. 4 also shows the narrowing apex feature.

Cross section T of FIG. 2 shows primary flutes 28 and secondary flutes 34 toward the proximal end 16 of shaft 12. The flutes are similar in shape and size, although primary flutes 28 appear to be slightly more pronounced or larger than secondary flutes 34. This is, again, a design consideration that those of ordinary skill in the art would understand can be manipulated based on the ultimate design needs.

Extending distally down shaft 12, cross section U shows that secondary flutes 34 begin to taper longitudinally. Cross sections V and W show further distal longitudinal tapering of the secondary flutes 34, in addition to a narrowing apex. Cross sections X-Z show that secondary flutes 34 eventually taper down to a sight ridge 32, and in some embodiments, secondary flutes 34 may taper out completely. In this or in other embodiments, the primary flutes 28 may form an outer profile 50 that is substantially constant at cross sections T, U, and V such that outer profile is a substantially cylindrical. If desired, outer profile 50 may begin to slightly taper as it extends longitudinally and distally, e.g., at cross section W, there may be the beginning of a longitudinal taper. (There is also no requirement that stem 10 have a length long enough to support each of cross sections T-Z. It is possible to form a shorter stem that ends at, for example, cross-section W, if desired. Longer stems are also possible.)

FIG. 2 shows a preferred embodiment of a longitudinal tapering scheme, but it should be understood that any form of tapering, whether more pronounced and drastic or more gentle and slight, is considered within the scope of this invention.

Although various embodiments have been described and any combination of primary flutes 28, secondary flutes 34, outer profiles and inner profiles are possible and considered within the scope of this invention, a particularly preferred embodiment of the invention features cross-sectionally tapered primary flutes that form an outer profile 50 that remains substantially contrast throughout the length of the stem (at least until it reaches the distal portion 18 of the stem), a longitudinally tapered core 52 that tapers as it extends toward the distal end 18 of the stem, and cross-sectionally tapered secondary flutes 34 that longitudinally taper as they extend toward the distal end 18 of the stem.

One or more of the flutes on stem 10 may be provided with a bone in-growth or on-growth feature. This may be a roughened surface, metallic beads, a grit blasted surface, a porous surface, a hydroxyapatite or any other bone growth-promoting substance coating, combinations of any of these features, and so forth. This allows the bone into which the stem is implanted to integrate with the stem 10 or otherwise grow into the flutes 20 for increased strength and stability.

Providing a longitudinally tapered core 52 on stem 10 offers a number of advantages. Without wishing to be bound to any theory, one advantage may be that there is increased surface area for stabilization and bone on-growth or in-growth. This tapering also provides a relative flexibility to the stem that mimics the slight flexibility of bone. A tapered core also allows more area for the flutes to engage with bone, more fully securing the stem into place and making the most advantage of strong distal bone.

Providing longitudinally tapering secondary flutes 34 (or in other embodiments, stepped down secondary flutes 34) on stem 10 also offers a number of advantages. While not wishing to be bound to any theory, it is believed that one advantage of tapered secondary flutes 34 is that they provide additional surface area on the stem 10 for bone on-growth. Another advantage may be that the distal longitudinal tapering of secondary flutes 34 provides a wedge-like surface (i.e., at the narrowing apex the tapering flute) that can grab the sides of the intramedullary canal for enhanced stability. One potentially useful analogy may be to compare the resulting wedge-shaped apex surface of secondary flute 34 to a wedge-shaped door stop that can be lodged underneath a door to support it in a particular position. As the secondary flutes 34 engage with bone when the stem 10 is being inserted, the flutes cut and compress the bone, securing the stem in place. (Various embodiments of the stem 10 may be used with or without bone cement.) The primary flutes 28 also provide this stabilization function.

Another optional feature of certain embodiments of the present invention is that in lieu of the traditional bowing or distal anterior chamfering found in some longer stems, the present stem design may have a transitional region 60 that leads to a downsized section 62, as shown in FIG. 5. In this embodiment, the transitional region 60 separates a portion of the shaft having a first profile 64 and a portion of the shaft having a different, smaller profile (which in this case, is the downsized region 62). The transition region 60 may have an outer profile that is substantially cylindrical (and just smaller than the first profile 64) or it may have an outer profile with a taper. Any other profile geometry could be used as is considered within the scope of this invention, for example parabolic, trumpet-shaped, bell-shaped, a stepped or sawtooth configuration, one or more ledges (that may be any angle, such as, for example, 90 degree transition or angled ledge), and so forth. The first profile area 64 is preferably substantially cylindrical. This feature may be provided with or without the above-described flutes.

Figure 6:
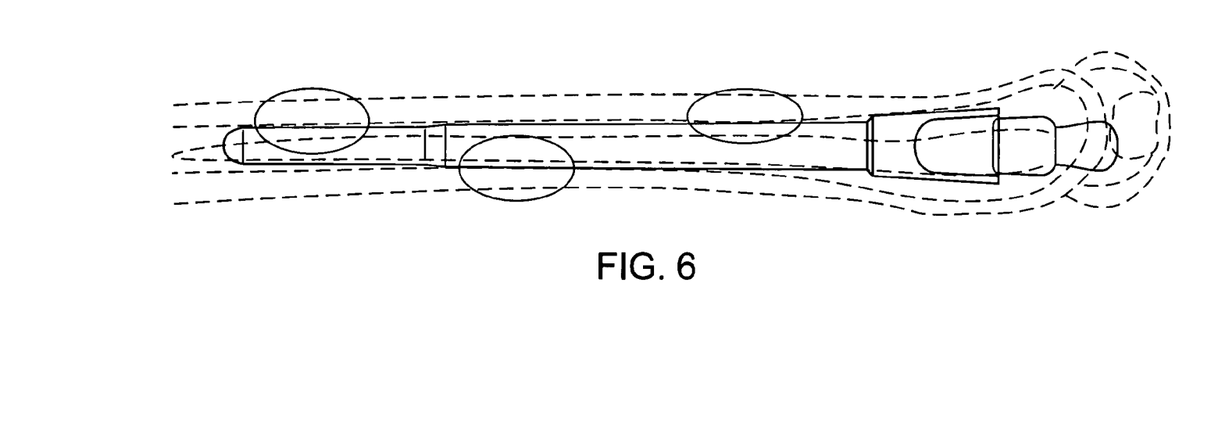
FIG. 6 shows a side plan view of the fixation points of the stem of FIG. 5.

The transitional region 60, if there is one, may be tapered, parabolic, stepped, or any other geometry, including those described above. Due to the transitional and downsized distal geometry, the fit obtained inside the intramedullary canal will be stable three-point fixation, as shown by the circled regions in FIG. 6. Using the transitional region 60 and the downsized cylindrical section 62 geometry to fit around the natural bow of the patient's femur provides the surgeon with near-infinite options for stem and neck fit. The transitional region 60 may also provide additional axial stability depending on the reaming procedure.

If desired, the transitional region/downsized cylindrical stem design configuration could also be used with a traditional-style bowed stem. Typically, a surgeon will over-ream (by 1 mm, for example, over the profile of the stem) when using a bowed stem prosthesis to mitigate the potential of a femoral fracture upon stem insertion. By downsizing the stem in the distal bowed region, the surgeon's technique is simplified because the stem is undersized in the critical region of the bow. Over-reaming is not necessary, as the surgeon can ream to the same profile as the proximal portion of the stem to achieve greater fixation proximally while facilitating insertion of the long bowed stem.

An alternate transition region 60 embodiment may be provided on a shaft with a first profile 64, but where the transition region 60 itself forms the remainder of the shaft. In other words, a separate downsized region 62 is not required. In this embodiment, the transition region 60 is preferably a tapered section.

In further embodiments, the stem flexibility may be enhanced by adding other distal features such as slots in one direction or multiple directions. A multi-directional slot may collapse and create a self-forming tapered section. Depending on reaming technique, these slots can be used for enhanced axial stability. The slot embodiment may be used in conjunction with either the fluted stem design, the transitional stem design, or both.

Stems 10 according to various embodiment of this invention may be manufactured by producing a tapered core stem and maintaining a cylindrical outer profile via the flutes 20. The resulting flutes can be parallel sided or tapered. They may be provided in any number and shape. The flutes may be of consistent height or may differ in height or level such that the stem has secondary or tertiary flutes (or even more options) of various heights for different engagement levels. The flutes may also vary in length and/or width.

In a particularly preferred embodiment, there are eight primary flutes 28 and eight secondary flutes 34. There may be more or fewer numbers of each type of flute. The outer profile 50 (or contact surface) of the stem 10 can be cylindrical or any other relatively constant multi-sided shape, such as rectangular, oval, an oblong cross sectional shape, or any other shape that will provide the desired stability.

The stem may be made from any biocompatible material that has sufficient strength to withstand the patient's weight, examples of which include titanium, titanium alloys, stainless steel, stainless steel alloys, and other surgical grade material.

The tapered core is particularly preferred to be used in connection with stems of this invention. However, the location at which the taper begins along the stem length can be modified to provide additional axial support and any other desired characteristics.

Surgical Method:

During a total hip replacement, the surgeon takes a number of measurements to ensure proper prosthesis selection, limb length and hip rotation. After making the incision, the surgeon gains access to the joint and pushes the femur out of the socket, exposing the joint cavity. The deteriorated femoral head is removed and the acetabulum is prepared by cleaning and enlarging with circular reamers of gradually increasing size. The new acetabular shell is implanted securely within the prepared hemispherical socket. The plastic inner portion of the implant is placed within the metal shell and fixed into place. If the surgery is a revision surgery, the previous implant will be removed and the bone prepared accordingly.

Next, the femur is prepared to receive the stem. The inside of the femoral canal is cleaned and enlarged by broaches, reamers, and other tools, creating a cavity that is smaller than, but that corresponds to the outer profile 50 of the implant stem 10. That outer geometry is dictated by the size and shape of the stem 10 and should be prepared so that the stem 10, upon insertion, will fit tightly and securely in the canal. The stem may be placed in the canal with or without cement. (Typically, the flute geometry of the present invention would not be used with cement, although it would be possible.) To supplement this joining, cables, bolts, grips, or struts could be used, examples of which are described in Application Publication Numbers 2004/0097942 and 2004/0087954. If a modular body, neck, stem, or any combination thereof is to be used to provide the upper stem portion of the implant, the proper size is selected and attached. Finally, the ball is seated within the cup so the joint is properly aligned and the incision is closed.

It should be noted that stems according to various embodiments of the invention may be used in impaction or compaction grafting procedures, where the surgeon uses a bone graft or like substance to rebuild bone before implanting the stem. For the same reason that the flutes engage the patient's intramedullary canal and provide a stable construct, they will similarly engage a bone graft.

Upon implantation, the tapered core 52 provides enhanced flexibility over a traditional cylindrically-shaped stem (fluted or solid), which should minimize some clinical consequences of stiff-stems such as thigh pain and osteolysis. Once the bone begins to grow onto the inner tapered core 52, the stem 10 should behave similar to a traditional tapered stem, where the body weight is transferred onto the femur more efficiently by a compressive force component. Clinical studies have indicated that a grit-blasted titanium stem surface will promote bone on-growth within weeks of surgery. Most patients are able to bear weight on the operated leg within several days of surgery.

In summary, some of the major advantages of the fluted, tapered-core, cylindrical stem design embodiment described are the ease of implantation, stem flexibility, and effective loading stress distribution. Similar advantages will be found with the transitional region embodiment. Because the distal stem can be prepared with traditional cylindrical reamers and consistently seated longitudinally within the canal, the surgical technique should be easier for the surgeon and more reproducible than with traditional tapered-style stems. This stem design is more flexible than traditional cylindrical stems and should exhibit more favorable stress distribution to the bone, resulting in less stress-shielding and osteolysis.

Changes and modifications, additions and deletions may be made to the structures and methods recited above and shown in the drawings without departing from the scope or spirit of the invention and the following claims.

What is claimed is:

1. An intramedullary implant, comprising:
   (a) a stem having a shaft with a longitudinal length, a proximal end, and a distal end;
   (b) a series of flutes disposed on the length of the shaft, the flutes comprising apexes and bases;
   (c) the flute apexes defining an outer profile of the shaft;
   (d) the flute bases defining a core of the stem, wherein the core tapers toward the distal end of the stem,
   (e) valleys between the bases with slight ridges near the distal end, wherein the ridges increase in size to form wedges as the ridges extend proximally up the stem.

2. The intramedullary implant of claim 1, wherein the stem is modular.

3. The intramedullary implant of claim 1, wherein the stem further comprises an upper stem portion comprising a body, a neck, and a ball, or combinations thereof.

4. The intramedullary implant of claim 1, wherein the flutes are cross-sectionally tapered, substantially-parallel sided, or any combination thereof.

5. The intramedullary implant of claim 1, wherein the flutes are longitudinally tapered.

6. The intramedullary implant of claim 1, wherein the flutes, the wedges, or both, have narrowed apexes.

7. The intramedullary implant of claim 1, wherein the wedges are cross-sectionally tapered, substantially-parallel sided, or any combination thereof.

8. The intramedullary implant of claim 1, wherein the stem has a bone on-growth or bone in-growth feature.

9. The intramedullary implant of claim 8, wherein the bone on-growth or bone in-growth feature comprises a roughened surface, metallic beads, a grit blasted surface, a porous surface, a hydroxyapatite or any other bone growth-promoting substance coating, or combinations thereof.

10. The intramedullary implant of claim 1, wherein the intramedullary implant is adapted to be implanted into a femur.

11. The intramedullary implant of claim 1, wherein the outer profile is substantially cylindrical at least some point along the shaft.

12. An intramedullary implant, comprising: (a) a stem having a proximal end, a distal end, and a longitudinal length; (b) primary and secondary flutes disposed along the longitudinal length, each of the primary and secondary flutes having an apex, the apexes of the primary flutes define an outer profile that is substantially cylindrical, the apexes of the secondary flutes being shorter than the apexes of the primary flutes such that the secondary flutes do not extend to the outer profile of the primary flutes wherein the primary flutes extend the substantial length of the stem, and wherein the secondary flutes taper longitudinally toward the distal end of the stem.

13. The intramedullary implant of claim 12, wherein the apexes of the primary flutes and secondary flutes have bases that define a tapered stem core that tapers distally.

14. The intramedullary implant of claim 12, wherein the stem is modular.

15. The intramedullary implant of claim 12, wherein the primary and secondary flutes are cross-sectionally tapered, substantially-parallel sided, or combinations thereof.

16. The intramedullary implant of claim 12, wherein the stem has a bone on-growth or bone in-growth feature.

17. The intramedullary implant of claim 16, wherein the bone on-growth or bone in-growth feature comprises a roughened surface, metallic beads, a grit blasted surface, a porous surface, a hydroxyapatite or any other bone growth-promoting substance coating, or combinations thereof.

18. The intramedullary implant of claim 12, wherein the intramedullary implant is adapted to be implanted into a femur.

* * * * *

UNITED STATES PATENT AND TRADEMARK OFFICE
CERTIFICATE OF CORRECTION

PATENT NO. : 7,575,603 B2  Page 1 of 1
APPLICATION NO. : 11/139926
DATED : August 18, 2009
INVENTOR(S) : Bergin et al.

It is certified that error appears in the above-identified patent and that said Letters Patent is hereby corrected as shown below:

On the cover page,

[*] Notice:    Subject to any disclaimer, the term of this patent is extended or adjusted under 35 USC 154(b) by 392 days.

Delete the phrase "by 392 days" and insert -- by 710 days --

Signed and Sealed this

Eighteenth Day of May, 2010

David J. Kappos
*Director of the United States Patent and Trademark Office*